US009297085B2

(12) United States Patent
Kitaori et al.

(10) Patent No.: US 9,297,085 B2
(45) Date of Patent: Mar. 29, 2016

(54) MEMBRANE-ELECTRODE ASSEMBLY, ELECTROLYTIC CELL EMPLOYING THE SAME, ELECTROLYTIC-WATER SPRAYER, AND METHOD OF STERILIZATION

(71) Applicants: PERMELEC ELECTRODE LTD., Fujisawa-shi, Kanagawa (JP); Institute of National Colleges of Technology, Japan, Hachioji-shi, Tokyo (JP)

(72) Inventors: Noriyuki Kitaori, Tokyo (JP); Kota Sekido, Kanagawa (JP); Tomoyasu Shibata, Kanagawa (JP); Tomohisa Suzuki, Kanagawa (JP); Masashi Tanaka, Kanagawa (JP); Tsuneto Furuta, Kanagawa (JP); Yoshinori Nishiki, Kanagawa (JP)

(73) Assignees: DE NORA PERMELEC LTD., Kanagawa (JP); Institute of National Colleges of Technology, Japan, Hachoji-shi (JP)

( * ) Notice: Subject to any disclaimer, the term of this patent is extended or adjusted under 35 U.S.C. 154(b) by 0 days.

(21) Appl. No.: 14/256,605

(22) Filed: Apr. 18, 2014

(65) Prior Publication Data
US 2014/0224649 A1   Aug. 14, 2014

Related U.S. Application Data

(62) Division of application No. 12/260,724, filed on Oct. 29, 2008, now abandoned.

(30) Foreign Application Priority Data

Nov. 15, 2007   (JP) .................................. 2007-296769
Oct. 15, 2008   (JP) .................................. 2008-266158

(51) Int. Cl.
*C25D 17/00* (2006.01)
*C25B 9/08* (2006.01)
(Continued)

(52) U.S. Cl.
CPC ................. *C25B 9/08* (2013.01); *A61L 2/0088* (2013.01); *A61L 2/18* (2013.01); *A61L 2/183* (2013.01);
(Continued)

(58) Field of Classification Search
CPC .............. C25B 11/02; C25B 9/08; C25B 1/13
See application file for complete search history.

(56) References Cited

U.S. PATENT DOCUMENTS 3,984,303 A   10/1976   Peters et al.
4,260,468 A   4/1981   Bradley
(Continued)

FOREIGN PATENT DOCUMENTS

EP   1 741 676 A2   1/2007
JP   2000-079393 A   3/2000
(Continued)

OTHER PUBLICATIONS

Chinese Office Action dated Jan. 28, 2011 issued in counterpart Chinese Patent Application No. 200810171587.7.
(Continued)

*Primary Examiner* — Ibrahime A Abraham
(74) *Attorney, Agent, or Firm* — Sughrue Mion, PLLC

(57) ABSTRACT

The present invention provides a membrane-electrode assembly which includes: at least one rod-form or tubular electrode; a tubular diaphragm disposed around the periphery of the electrode; and a wire-form counter electrode disposed around the periphery of the diaphragm, the diaphragm being fixed to the rod-form or tubular electrode with the wire-form counter electrode to thereby form an electrode chamber having a gas/liquid passage between the diaphragm and the rod-form or tubular electrode.

5 Claims, 6 Drawing Sheets

(51) Int. Cl.
  *A61L 2/00* (2006.01)
  *A61L 2/18* (2006.01)
  *C02F 1/461* (2006.01)
  *C25B 1/13* (2006.01)
  *C25B 11/02* (2006.01)
  *C02F 1/66* (2006.01)

(52) U.S. Cl.
  CPC ............... *A61L 2/186* (2013.01); *C02F 1/4618* (2013.01); *C25B 1/13* (2013.01); *C25B 11/02* (2013.01); *A61L 2202/11* (2013.01); *A61L 2202/15* (2013.01); *C02F 1/66* (2013.01); *C02F 2001/46142* (2013.01); *C02F 2001/46152* (2013.01); *C02F 2001/46161* (2013.01); *C02F 2201/003* (2013.01); *C02F 2201/4611* (2013.01); *C02F 2201/46115* (2013.01); *C02F 2201/46125* (2013.01); *C02F 2201/46145* (2013.01); *C02F 2301/026* (2013.01); *C02F 2305/04* (2013.01)

(56) References Cited

U.S. PATENT DOCUMENTS

| | | |
|---|---|---|
| 6,210,643 B1 | 4/2001 | Shiota |
| 6,942,767 B1 | 9/2005 | Fazzina et al. |
| 2007/0023273 A1 | 2/2007 | Kitaori et al. |
| 2007/0166589 A1 | 7/2007 | Nakanishi et al. |

FOREIGN PATENT DOCUMENTS

| | | |
|---|---|---|
| JP | 2000-197889 A | 7/2000 |
| JP | 2001-276826 A | 10/2000 |
| JP | 2005-177597 A | 7/2005 |
| JP | 2006-346203 A | 12/2006 |
| JP | 2007-203157 A | 8/2007 |
| KR | 10-2006-0131687 A | 12/2006 |
| TW | 200719930 A | 6/2007 |

OTHER PUBLICATIONS

Extended Search Report issued by the European Patent Office in counterpart application No. 08018895.6 dated Jun. 17, 2009.
Japanese Office Action issued in Application No. 2008-266158; dated Dec. 6, 2010.
Korean Office Action issued in counterpart Korean Application No. 10-2008-0106850, on Mar. 31, 2012.
Machine Translation of JP 2007-203157.
Office Action dated Nov. 20, 2012, issued by the Taiwanese Intellectual Property Office in counterpart Taiwanese Patent Application No. 097141733.
Office Action issued Jun. 26, 2012 by the Intellectual Property Office in counterpart Taiwanese Application No. 05161/10120622400.
Office Action issued Mar. 31, 2012 by the Republic of Korea Patent Office in counterpart Korean Application No. 10-2008-0106850.

MEMBRANE-ELECTRODE ASSEMBLY, ELECTROLYTIC CELL EMPLOYING THE SAME, ELECTROLYTIC-WATER SPRAYER, AND METHOD OF STERILIZATION

CROSS REFERENCE TO RELATED APPLICATION

This is a Divisional of application Ser. No. 12/260,724 filed Oct. 29, 2008, claiming priority based on Japanese Patent Application Nos. 2007-296769 filed Nov. 15, 2007 and 2008-266158 filed Oct. 15, 2008, the contents of all of which are incorporated herein by reference in their entirety.

FIELD OF THE INVENTION

The present invention relates to a membrane-electrode assembly for yielding electrolytic water to be used for sterilization, cleaning, etc., an electrolytic cell employing the assembly, an electrolytic-water sprayer including any of the electrolytic cell, and a method of sterilization using these.

BACKGROUND OF THE INVENTION

Bactericide/Disinfectant Solution:

Chlorine compound bactericides such as sodium hypochlorite, calcium hypochlorite, and sodium dichloroisocyanurate have been extensively used as bactericides/disinfectants in a wide range of environments. Of these, hypochlorites including sodium hypochlorite are in general use from the standpoints of cost and effect. However, many proposals have been made for attaining improvements in the bactericidal/disinfectant effect thereof which are required in various fields including the clinical field and the food industry (see, for example, JP-A-2001-253803, JP-A-2001-342496, and JP-A-2002-145710).

Usually, such bactericides/disinfectants are prepared by adding the respective ingredients for constituting the composition to water or by mixing aqueous solutions containing the respective ingredients.

Use of Electrolytic Water as Substitute:

However, the use of chlorine compound bactericides in large amounts arouses troubles. For example, in factories and retail stores where food materials are handled in large quantities, cleaning with a sodium hypochlorite solution having a concentration exceeding 100 ppm is conducted. This cleaning, however, is regarded as problematic because it not only spoils the flavors of the food materials but also arouses a hazard (increase in THM).

Mainly for the purpose of eliminating those problems, investigations have been diligently made on the usefulness of electrolytic water, i.e., water yielded by electrolysis, in the agricultural, food, clinical, and other fields. The substitution of electrolytic water or ozonized water is proceeding mainly in Japan. Electrical energy, which is a clean energy, can be utilized to synthesize hydrogen, oxygen, ozone, hydrogen peroxide, etc. through chemical reactions on electrode surfaces while regulating the reactions. It is known that oxidation reactions especially on the anode yield oxidizing agents effective in water treatments (effective chlorine and peroxides such as ozone) and further generate active species such as OH radicals in some cases (Kyōsansei Denkaisui No Kiso Chishiki (Fundamental Knowledge of Strongly Acidic Electrolytic Water), Ohm-sha, Ltd.).

Attention is being directed to the excellent bactericidal/disinfectant activity of electrolytic water, and investigations are being made on the use of the water in clinical activities and in the home. Examples of the uses thereof which are being investigated include the sterilization/disinfection of diseased parts, incised parts, percutaneous openings for stationary catheters, etc. and the sterilization/disinfection of domestic utensils or articles, such as kitchen utensils, baby articles, and furniture, and house equipments such as the toilet facilities and bathtub. Such electrolytic water is obtained by electrolyzing water (water to be electrolyzed) to which a solute that generates ions upon dissolution, e.g., sodium chloride, has been added optionally together with an acid for pH regulation.

Kinds of Electrolytic Water:

Besides being used as a food additive, electrolytic water is usable also in other applications. In an electrolytic cell containing water only, the following anode reaction proceeds to evolve oxygen according to formula (1). However, depending on the catalyst and electrolysis conditions, ozone is yielded according to formula (2) and ozonized water containing the ozone dissolved therein can be synthesized.

$$2H_2O = O_2 + 4H^+ + 4e \quad (1)$$

$$3H_2O = O_3 + 6H^+ + 6e \quad (2)$$

In the case where the water contains hydrochloric acid or chloride ions added thereto, hypochlorous acid is yielded according to formulae (3) and (4). In the case where the water contains sulfuric acid, the reaction represented by formula (5) proceeds to yield persulfuric acid.

$$Cl^- = Cl_2 + 2e \quad (3)$$

$$Cl_2 + H_2O = HCl + HClO \quad (4)$$

$$2SO_4^{2-} = S_2O_8^{2-} + 2e \quad (5)$$

When carbonate ions are present, the reaction represented by formula (6) proceeds to yield percarbonic acid.

$$2CO_3^{2-} = C_2O_6^{2-} + 2e \quad (6)$$

Through cathode reactions, it is possible to synthesize hydrogenous water, which is water containing excess hydrogen dissolved therein, alkali ion water, and the like according to formulae (7) and (8).

$$2H^+ + 2e = H_2 \quad (7)$$

$$2H_2O + 2e = H_2 + 2OH^- \quad (8)$$

Furthermore, hydrogen peroxide or the like can also be synthesized.

As shown above, electrolytic water containing two or more peroxides can be produced with electrolytes suitably selected, besides the acid waters which have been approved as food additives.

Features of Electrolytic Water: (reference: Mizu No Tokusei To Atarashii RiyōGijutsu (Characteristics of Water And Novel Application Technology), 2004, NTS Inc.)

There are the following three kinds of electrolytic water which have been approved as food additives.

a) Weakly alkaline electrolytic hypochlorite water (additive name, electrolytic sodium hypochlorite water; 20-200 ppm; pH>7.5; yielded from 0.2-2% aqueous sodium chloride solution using no diaphragm)

b) Slightly acid electrolytic water (additive name, slightly acid hypochlorous acid water; 10-30 ppm; pH=5-6.5; yielded from 2-6% hydrochloric acid using no diaphragm)

c) Strongly acid electrolytic water (additive name, strongly acid hypochlorous acid water; 20-60 ppm; pH<2.7; yielded as anolyte water from 0.2% or lower aqueous sodium chloride solution in diaphragm type cell)

The acid waters among those kinds of electrolytic water have, for example, the following merits.

(1) The acid waters are superior in safety because THMs are less apt to generate under acid conditions.

(2) Resistant bacteria are less apt to generate and on-site management is easy.

(3) The waters can be used for treatment in combination with the alkaline electrolytic water.

(4) The waters can be utilized like tap water and impart no remaining odor to the hands or fingers.

(5) Use of the waters just before suffices (sterilization time is short).

In the conventional treatment with sodium hypochlorite solutions, use of this chemical having a concentration up to 200 ppm as a food additive has been approved. However, the chemical spoils the flavor and has a residual tendency. In contrast, the electrolytic water of those kinds has a high bactericidal effect even in a low concentration and is beneficial, although use thereof necessitates an initial investment in the apparatus.

Features of Ozonized Water:

The long-term use of hypochlorites has yielded bacteria resistant to these chemicals, and there is a doubt about the bactericidal effect thereof. On the other hand, ozonized water has been placed on food additive lists and has gained approval of FDA (Food and Drug Administrations) of U.S.A. (2001) for use as a bactericide in food storage/production steps. Ozonized water has already come into many practical uses for sterilization in food factories and the sterilization of foods themselves. Recently, attention is focused on the fact that ozonized water is equal or superior in effect to sterilizing waters heretofore in use also in clinical fields such as dermatology, ophthalmology, and dentistry and is effective in reducing the burden to be imposed on the living body.

Ozonized water has, for example, the following merits.

(1) The bactericidal effect of ozone (OH radicals) is based on the oxidative destruction of cell walls and this indiscriminate activity is thought not to generate resistant bacteria.

(2) Ozone does not have a residual tendency.

When ozonized water is used in combination with an oxidizing agent having a residual tendency (e.g., a hypochlorite, persulfate, or percarbonate) according to need, a more effective sterilization treatment is possible.

Conventional Process for Producing Ozonized Water:

Ozonized water has conventionally been produced generally with a discharge type ozone gas generator. Ozonized water having a concentration of several parts per million parts can be easily produced by the process, and is being utilized in the fields of water purification treatment and food cleaning. However, the apparatus has been unsuitable for use as a handy ozonized-water production apparatus having excellent instant-response characteristics and yielding high-concentration ozonized water, for the following reasons.

(1) The ozonized-water production necessitates two steps, i.e., first generating ozone as a gas and then dissolving the gas in water.

(2) The ozonized water has a lower concentration than that produced by the electrolytic process which will be described later and, hence, the water should be produced through high-pressure injection into water and dissolution therein.

(3) The power source for ozone generation has a high voltage and a high frequency, making it difficult to attain a size reduction.

(4) In the ozonized-water production apparatus based on a discharged, a certain time period (stand-by time of several minutes) is required for the ozone gas generation ability to become stable and it is difficult to instantaneously prepare ozonized water having a certain concentration.

Electrolytic Ozone Production Process:

The electrolytic process is inferior to the discharge process in electric power consumption rate. However, a feature of the electrolytic process resides in that high-concentration ozone gas and ozonized water can be easily obtained. The electrolytic process is hence in general use in special fields such as, e.g., the cleaning of electronic parts. Since a direct-current low-voltage power source is employed because of the principle of the process, the apparatus is excellent in instant-response characteristics and safety and is expected to be used as a small ozone gas generator or a small ozonized-water production apparatus. According to applications, a driving mode can be selected from battery driving, power-generator driving, and AC-DC conversion driving.

For efficiently generating ozone gas, it is indispensable to select a proper catalyst and electrolyte. Known electrode materials include noble metals such as platinum, α-lead dioxide, β-lead dioxide, glassy carbon impregnated with a fluorocarbon, and diamond. As an electrolyte, use has been made of an aqueous solution containing sulfuric acid, phosphoric acid, fluorinated groups, or the like. However, these electrolytes have poor handleability and are not in extensive use. A water electrolysis cell which employs a solid polymer electrolyte as a diaphragm and in which pure water is used as a raw material is easy to manage in that respect and is in general use (*J. Electrochem. Soc.*, 132, 367 (1985)). When lead dioxide, which has been employed as a catalyst, is used, ozone gas having a concentration as high as 12% or above is obtained.

In the system called a direct synthesis system, the solution located around an electrode is caused to flow at a sufficient velocity to thereby take out the ozone as ozonized water before gasifying (JP-A-8-134677). Furthermore, in the case where raw water other than pure water is supplied to the electrolytic system, the activity of the noble-metal electrode catalyst itself is influenced by the quality of the water. Care should hence be given to the fact that electrolytic performances such as life and efficiency fluctuate. JP-A-9-268395 discloses that conductive diamond is useful as an electrode for producing functional water (containing ozone).

Development of Small Apparatus:

Portable or small electrolytic-water production/ejection apparatus have been proposed in order to more easily conduct sterilization/disinfection or the like in clinical activities or in the home (see patent documents 1 to 3). Such small apparatus may be extensively used for the deodorization, sterilization, or bleaching of indoor facilities, water-related facilities, tableware, garments, etc. in the home or for business purposes or for the sterilization or disinfection of the human body, e.g., the hands or fingers, etc.

Patent Document 1: JP-A-2000-79393
Patent Document 2: JP-A-2000-197889
Patent Document 3: JP-A-2001-276826

Besides those, the following are known: JPA-2004-129954 (apparatus having a device which generates power necessary for electrolysis); JP-A-2004-130263 (apparatus in which the proportion of the capacity of the piston to the volume, sectional area, etc. of the cell cylinder part is a specific value); JP-A-2004-130264 (apparatus in which raw water for electrolysis comprising a pH regulator, surfactant, chlorine compound, and water is used to obtain electrolytic water having a pH of 3-8.5); JP-A-2004-130265 (the electrolytic water according to JP-A-2004-130264 is used in a foamed state); JP-A-2004-130266 (the direction of voltage application to the electrodes is changed alternately); JP-A-2004-148108 (the voltage to be applied to the electrodes is variable); JP-A-

2004-148109 (apparatus having electrodes in a suction passage); JP-A-2003-93479, JP-A-2003-266073, and JP-A-2002-346564 (separation type having a cylindrical electrode in a spraying part); and JP-A-2001-47048 (gun type prevented from being clogged during non-spraying period and equipped with a motor).

Known techniques intended to synthesize ozonized water include the following. JP-A-2000-169989 discloses a small electrolytic ozone generator which has a structure including an assembly composed of a solid cylindrical shaft and, wound on the shaft, a metal-gauze-like anode (platinum), an ion-exchange membrane, and a metal-gauze-like cathode and disposed in a water channel and in which the shaft has a thin groove formed therein. JPA-2001-198574 discloses a module for connection to piping which includes a solid cylindrical shaft and, fixed to the shaft, a porous anode, a solid polymer electrolyte (ion-exchange membrane), and a porous cathode and has a drain line capable of separately discharging the ozonized water to be synthesized at the anode and the hydrogen/hydrogen gas to be synthesized at the cathode. JP-A-2002-143851 discloses a method of water treatment with a double-pipe structure including a supporting cylindrical member having a through-hole and, wound on the cylindrical member, a cathode, a membrane, and an anode. In this method, hard-water components can be inhibited from depositing from tap water as raw water by passing a dilute aqueous solution of sodium chloride through the cylinder serving as a cathode chamber, and an ultraviolet treatment can also be conducted simultaneously. JP-A-2004-60010 and JP-A-2004-60011 disclose an ozonized-water production apparatus which is capable of separating a catholyte with an electrolytic cell equal to that described in JP-A-2000-169989 and of measuring the concentration of ozone with an electromotive-force measuring device disposed in the channel. JPA-2006-346203 discloses use of conductive diamond as an electrode and, in particular, discloses an electrolytic cell including a rod-form conductive-diamond electrode, a strip-form diaphragm member disposed around the electrode, and a wire-form counter electrode disposed on the diaphragm member. Furthermore, JP-A-2007-136356 discloses a structure including a cylindrical core member having grooves extending in the cylinder direction and, wound on the core member in the following order, a cathode, a membrane, and an anode.

SUMMARY OF THE INVENTION

Conventional small electrode assemblies and electrolytic cells employing the assemblies have had the following problems.

(1) Although use of an ion-exchange membrane or the like improves ionic conductivity and this is expected to increase electrolysis reaction efficiency, it has been difficult to join the membrane or the like with the electrodes.

(2) The membrane usually is nonporous and is used usually in combination with porous electrodes for facilitating the feeling of an electrolytic solution and removal of products. The shape of the electrode assembly is hence complicated.

(3) When the assembly is to be attached to an apparatus, the piping membranes are frequently cylindrical and, hence, the electrodes preferably have a shape suitable for the piping members, i.e., a rod-form or cylindrical shape. It has been necessary to employ an apparatus suitable for that shape.

(4) Although a platinum catalyst is excellent in the property of accelerating ozone generation, it is unstable and apt to be influenced by the raw water. There are cases where ozonized water having a concentration of several parts per million, which enables short-time sterilization, cannot be synthesized when tap water is used as it is.

(5) In yielding ozonized water, the hydrogen which has generated at the counter electrode is separated to increase partial pressure and this inevitably results in an increase in solute concentration. However, there has been no cell having a structure suitable for that.

If those problems are overcome, it is expected that the use of electrolytic water in the home, hospitals, nursing care facilities, etc. expands further.

An object of the invention is to provide a membrane-electrode assembly with which many of those problems can be eliminated and which can be easily produced and bring about high performance. Another object of the invention is to provide an electrolytic cell and an electrolytic-water sprayer, each employing the assembly, and a method of sterilization. The electrolytic-water sprayer of the invention electrolyzes a raw aqueous solution, and the electrolytic water thus yielded can be immediately utilized.

The invention first provides a membrane-electrode assembly which comprises:

at least one rod-form or tubular electrode;

a tubular diaphragm, preferably ion-exchange membrane, disposed around the periphery of the electrode; and a wire-form counter electrode disposed around the periphery of the diaphragm, the diaphragm being fixed to the rod-form or tubular electrode with the wire-form counter electrode to thereby form an electrode chamber having a gas/liquid passage between the diaphragm and the rod-form or tubular electrode.

The invention secondly provides a membrane-electrode assembly which comprises at least one rod-form or tubular electrode;

a tubular diaphragm disposed around the periphery of the electrode; and a porous counter electrode disposed around the periphery of the diaphragm, the diaphragm being fixed to the rod-form or tubular electrode with the porous counter electrode to thereby form an electrode chamber having a gas/liquid passage between the diaphragm and the rod-form or tubular electrode.

The invention thirdly provides a membrane-electrode assembly which comprises:

at least one rod-form or tubular electrode having a recessed part formed therein;

a tubular diaphragm disposed around the periphery of the electrode so as to form an electrode chamber having a gas/liquid passage between the diaphragm and the electrode; and a platy counter electrode disposed around the periphery of the diaphragm.

According to the invention, an electrolytic cell and an electrolytic-water sprayer each having the membrane-electrode assembly can be constituted. The electrolytic-water sprayer can be used to yield electrolytic water and eject the electrolytic water to a substance to sterilize it.

The invention will be explained below in detail.

The membrane-electrode assembly of the invention is characterized by being produced by disposing a tubular diaphragm, e.g., an ion-exchange membrane, around the periphery of a rod-form or tubular electrode, usually an anode (hereinafter referred to also as rod anode), disposing a wire-form or porous counter electrode, usually a wire-form or porous cathode, around the periphery of the membrane, fixing those members with the cathode so that the membrane is in contact with at least part of the anode and that the membrane is in contact with at least part of the cathode, and forming an anode chamber having a gas/liquid passage between the membrane and the anode and preferably among a plurality of anodes.

In the invention, an anode chamber separated from a cathode chamber by a diaphragm is formed to constitute an appropriate gas/liquid passage. By changing a water feed rate and current value, the concentration of an electrolytically yielded species in the electrolytic water can be regulated to a desired value.

In the following explanations, the rod electrode and the counter electrode are used as an anode and a cathode, respectively. In the invention, however, the rod electrode and the counter electrode may be conversely used as a cathode and an anode, respectively.

This membrane-electrode assembly can have a constitution including a rod anode, a sheet-form membrane disposed, in a tube-forming manner, around the periphery of the anode, and a wire cathode spirally wound thereon at an appropriate pitch. In this constitution, not only the rod anode, membrane, and wire cathode can be kept in partial contact with each other but also an anode chamber through which the liquid and the gas generated can move spirally can be formed between the rod anode and the membrane or among a plurality of rod anodes.

A membrane-electrode assembly having an ideal passage is obtained by suitably selecting the diameter and number of the rod anode, diameter of the tubular membrane, and material, thickness, and winding pitch of the wire cathode. In particular, by spirally winding the wire cathode at a pitch of 1-10 mm, an assembly having a suitable structure is obtained. It is especially preferred that the anode should be diamond, because this assembly can efficiently generate ozone, etc.

This membrane-electrode assembly can be used to constitute an electrolytic cell which includes a tube fixed to at least one of the openings of the anode chamber and one or two feeder terminals connected to the anode and/or the cathode.

Furthermore, by fixing a tube to the two openings of the anode chamber formed between the anode and the diaphragm and fixing the resultant member in a second tube having at least two openings, a cathode chamber can be formed between the cathode and the diaphragm. One or two feeder terminals are connected to the anode and/or cathode. Thus, an electrolytic cell can be constituted in which electrolysis is conducted while feeding raw water to one of the openings of the anode chamber and feeding raw water also to one of the openings of the cathode chamber according to need. Since the diaphragm has been deformed so as to spirally form the anode chamber between the diaphragm and the anode, the cathode chamber also has been spirally formed. Because of this, the gas and liquid present near the cathode in the cathode chamber can be caused to flow spirally. In this cell, acid water and alkaline water can be simultaneously synthesized in the anode chamber and the cathode chamber, respectively.

When the raw water is passed through the electrolytic cell and a voltage is applied to the cell, then the raw water comes into contact with the rod electrode and counter electrode in the electrolytic cell and is electrolyzed to yield electrolytic water.

This electrolytic cell is mounted in an electrolytic-water ejection apparatus including a vessel containing raw water and a head. When the raw water is sucked up and passed through the tube and a voltage is applied to the electrolytic cell, then the raw water comes into contact with the rod anode and the cathode in the electrolytic cell and is electrolyzed to yield electrolytic water. This electrolytic water is discharged outside in an atomized or liquid state through the nozzle of the head optionally with a power assist such as, e.g., a pump.

Alternatively, the electrolytic cell may be directly connected to a water supply line. When raw water is fed from the water supply line to the anode chamber or cathode chamber and electrolyzed while being fed, then the same active electrolytic water is yielded.

In those electrolytic cells, an active species such as ozone is efficiently synthesized in a high concentration to yield electrolytic water having a sterilizing/bleaching ability. The concentration of ozone or another species in the electrolytic water depends on the amount of raw water flowing through each chamber per unit time period. The area of the section through which raw water flows can be regulated by regulating the diameter and number of the rod anode, diameter of the tubular membrane, and winding pitch of the wire cathode. Thus, electrolytic water can be efficiently produced.

The method of the invention and the electrolytic-water sprayer of the invention can be extensively used for the deodorization, sterilization, or bleaching of indoor facilities, water-related facilities, tableware, garments, etc. in the home or for business purposes or for the sterilization or disinfection of the human body, e.g., the hands or fingers, etc. As apparent from the explanations given above, the term "sterilization" in the method of sterilization of the invention means any of acts such as deodorization, bleaching, and disinfection, besides sterilization.

In the invention, highly active electrolytic water such as the following can be yielded by regulating conditions.

(1) Alkaline electrolytic water (alkaline water containing hydrogen gas dissolved therein)

(2) Acid electrolytic water (electrolytic water containing two or more peroxides yielded by electrolyte selection; sulfuric acid salts, carbonic acid salts, and the like are usable besides chlorides)

(3) High-concentration ozonized water (this water has no residual tendency, has bactericidal activity at least 10 times the bactericidal activity of hypochlorite systems, and further has a bleaching effect; the ozone half-life is prolonged by some coexistent substances to attain improved persistency)

(4) Novel composite electrolytic water (having a novel sterilizing effect brought about by adding an organic acid or surfactant for pH regulation for the purpose of improving bactericidal activity or by adding an alcohol or the like for the purpose of, e.g., improving bactericidal activity or refreshing feeling)

In the membrane-electrode assembly produced by disposing, in a tube-forming manner, a sheet-form ion-exchange membrane or the like around the periphery of at least one rod electrode and disposing a wire-form counter electrode or a porous counter electrode therearound, the rod electrode, membrane, and counter electrode have been united together. Because of this, the assembly once produced can be easily handled. This assembly can be easily produced.

Gas/liquid passages suitable for use as an electrode chamber (or as an electrode chamber and a counter electrode chamber) are formed by regulating the diameter of the rod electrode, sectional shape of the electrode, diameter of the tubular membrane and winding pitch in the case of a wire-form counter electrode, or by selecting the diameter of the tube in which those members are disposed to form a counter electrode chamber, and further appropriately deciding the number of the rod electrode to be used. By changing the water feed rate and current value, the concentration of an electrolytically yielded species in the electrolytic water can be regulated to a desired value. The electrolytic water obtained is ejected to or sprayed over a substance to be sterilized, whereby the substance can be sterilized with the electrolytically yielded species contained in the desired concentration.

Figure 1:
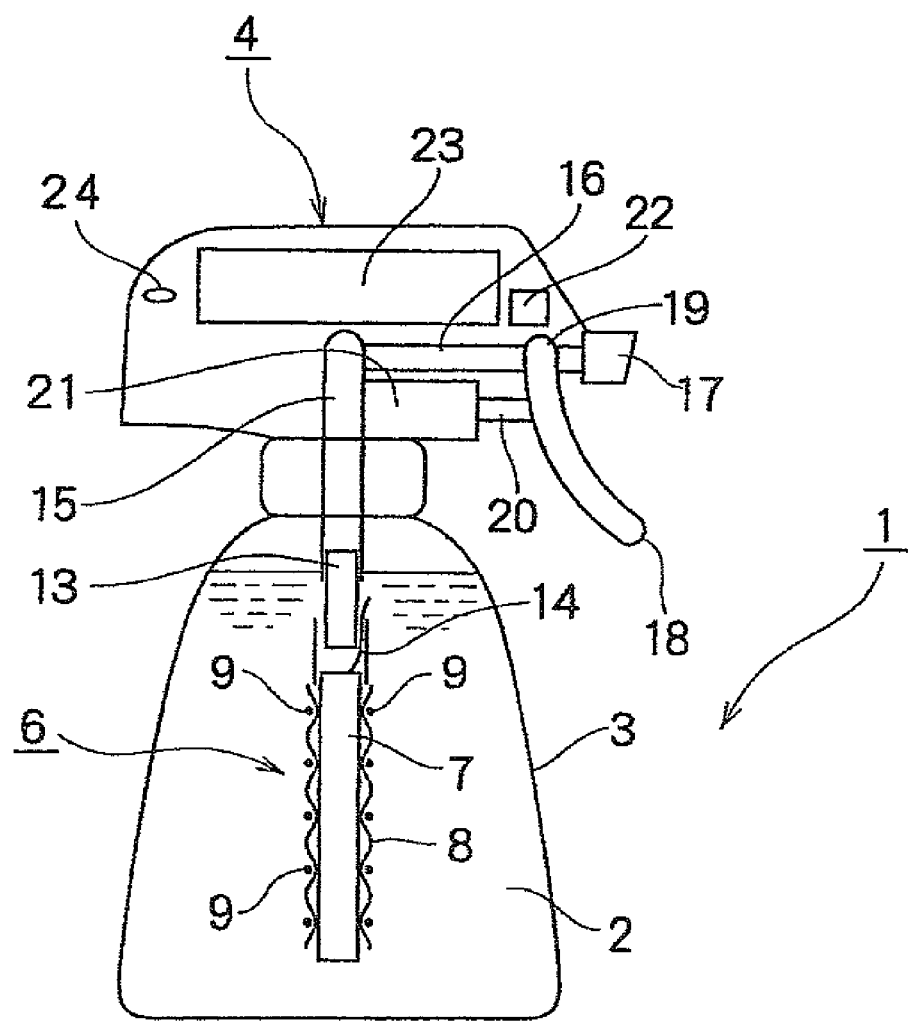
FIG. 1 is a front view illustrating an electrolytic-water sprayer as one embodiment of the invention.

The reference numerals used in the drawings denote the following, respectively.

1: Electrolytic-water sprayer
2: Raw water
3: Vessel
4: Head
6, 6a: Electrolytic cell
7, 7a: Anode
8, 8a: Diaphragm
9, 9a: Wire cathode
10, 10a: Anode chamber
15: Vertical pipeline
17: Spray nozzle
18: Trigger arm
22: Trigger-engaged switch
32: Electrolytic cell
33: Groove
34: Anode
35: Diaphragm
36: Porous cathode
37: Anode chamber
41: Diaphragm
43: Rod anode
44: Protrudent part
45: Anode chamber
46: Diaphragm
48: Tubular anode
49: Recessed part
50: Anode chamber

DETAILED DESCRIPTION OF THE INVENTION

The constituent elements of the invention will be explained below. However, the invention should not be construed as being limited to the following.

Anode and Anode Material:

Examples of anode catalysts for oxidation include lead oxide, tin oxide, noble metals such as platinum, DSAS (electrodes consisting mainly of a noble-metal oxide), carbon, and conductive diamond. From the standpoint of corrosion resistance, it is desirable to use as the electrode catalyst a noble metal such as platinum or iridium, an oxide of such a noble metal, or conductive diamond. The material to be used as an electrode base preferably has corrosion resistance from the standpoints of attaining a long life and preventing the surface to be treated from being fouled. It is desirable to use as the anode base a valve metal such as titanium or niobium or an alloy thereof. The anode material can be deposited on the surface of such a base having a shape heretofore in general use, such as a pipe or rod. Although the sectional shape thereof is desirably selected from circle, quadrangles, ellipses, and the like or from hollow cylinders, hollow prisms, and the like, it is not limited to these. To process the surface of a rod-form or cylindrical anode to impart recesses and protrusions thereto or, in the case of a hollow material, to form openings in the electrode surface is effective in enhancing gas/liquid permeability. A base obtained by rolling a metal gauze into a tubular form is also usable. The height of the recesses and protrusions is preferably 0.1-5 mm. Also usable is a base having a spiral groove extending in the cylinder direction.

By using a plural number of the anodes, instead of forming the recesses and protrusions on the surface of the anode, it is possible to easily and assuredly form liquid passages and enhance the gas/liquid permeability. Specifically, when rod-form or cylindrical anodes are lined up in rows, adjacent anodes are brought into close contact at one point and further the contact area of the anodes and the diaphragm decreases, thereby forming a large space among the anodes and between the anodes and the diaphragm. Therefore, liquid passages (anode chamber) can be formed without requiring troublesome operations such as surface processing of the anode.

The plural rod-form electrodes may be partly replaced with a member consisting of a base having no catalyst formed thereon. In this case, the member plays roles of forming a liquid passage and conducting a current to the other rod-form electrode(s).

The presence of a catalyst as part of the anode suffices, and the base may be partly exposed.

Diamond is regarded as a promising electrode material partly because the electrical conductivity thereof can be regulated by doping. Diamond electrodes are inert in water decomposition reaction. It has been reported that a diamond electrode in oxidation reactions yields ozone and hydrogen peroxide besides oxygen. When conductive diamond is used, electrolysis reactions proceed more readily and those peroxides as products of electrolysis are produced exceedingly efficiently. Furthermore, on the diamond electrode, OH radicals and oxidized forms of electrolytes are yielded besides the electrolytically yielded species shown above. Consequently, the sterilizing/bleaching effects of the OH radicals or oxidized forms and of the electrolytically yielded species can be synergistically utilized.

In the case where conductive diamond is used, examples of usable bases include Nb, Ta, Zr, Ti, Mo, W, graphite, and various carbides as well as Si (monocrystalline and polycrystalline). A suitable one can be selected according to applications.

Cathode Material, Cathode Feeder Wire:

Cathode reactions include hydrogen evolution as the main reaction. It is therefore preferred to use an electrode catalyst which is not embrittled by hydrogen. Examples of such preferred electrode catalysts include platinum group metals, nickel, stainless steel, titanium, zirconium, gold, silver, carbon, and diamond. As the cathode base, it is desirable to use stainless steel, zirconium, carbon, nickel, titanium, or the like.

The shape thereof preferably is a wire form. Besides being in a wire form, the cathode may be a metal gauze or foil which has been cut thinly. In the case of a wire form, the cathode may be a winding obtained by twisting plural thin filaments. This form is also preferred. In the case of using a wire cathode, there are cases where this wire cathode functions as a feeder. In the invention, this feeder is included in the wire cathode.

A porous metal gauze cathode may be rolled into a tubular form and deposited around the periphery of the ion-exchange membrane or the like. Examples of the porous cathode include expanded meshes and punching metals, besides metal gauzes. In the case of using these materials, it is desirable to form recesses and protrusions on the surface of the anode to thereby form an anode chamber between the ion-exchange membrane and the anode. However, an anode chamber may be formed by modifying such a porous cathode only and partly protruding the diaphragm toward the anode.

A diaphragm, e.g., an ion-exchange membrane, in which a catalyst layer has been formed beforehand on one side thereof may be disposed so that the side having the catalyst faces outward. This constitution is preferred because the electrolytic cell can have an even current distribution and a reduction in cell voltage can hence be attained. For forming the catalyst layer, existing techniques can be used, such as electroless plating and PVD. In this case, a metal wire serving also as a feeder is wound thereon. Preferred examples of feeder wire materials include platinum group metals, nickel, iron, copper, silver, gold, stainless steel, titanium, and zirconium.

Diaphragm Material:

As the diaphragm can be used an ion-exchange membrane or a neutral membrane. Usually, an ion-exchange membrane is used.

A diaphragm not only prevents substances yielded at the anode or cathode from being consumed at the opposed electrode, but also has the function of enabling electrolysis to proceed speedily even when a liquid having a low conductivity is used. Use of a diaphragm is therefore preferred when a raw material having poor conductivity, such as pure water, is used. In the case of using an ion-exchange membrane, it may be either a fluororesin membrane or a hydrocarbon resin membrane. However, the former membrane is preferred from the standpoint of resistance to corrosion by ozone and peroxides. The thickness of the membrane is preferably 0.1-1 mm.

In the case where a wire cathode is wound on the membrane to form a spiral passage, it is preferred to use as the membrane a commercial membrane containing reinforcing fibers and having high mechanical strength.

It is preferred to form the diaphragm into a tubular shape beforehand. This can be easily accomplished with a precursor resin having thermoplasticity by a known tube-forming processing technique. With respect to the diaphragm, one containing reinforcing fibers is preferred. Use may be made of a method in which a membrane in a sheet form is rolled into a tube and then bonded. In the case of a fluororesin ion-exchange membrane, use can be made of a method in which edge parts of the membrane are superposed and then thermally fusion-bonded together or fixed to each other with an adhesive. In the thermal fusion bonding, appropriate ranges of the processing temperature and the areal pressure are 200-350° C. and 2-20 kg/cm$^2$, respectively. An appropriate range of the processing time period is from 1 second to 1 minute. For increasing bonding strength and attaining more complete bonding, it is preferred that a narrow strip of a fluororesin membrane containing no reinforcing fibers be interposed in bonding the ion-exchange membrane.

To form recesses and protrusions on the membrane surface is preferred because this can enhance gas/liquid permeability.

Membrane-Electrode Assembly:

The length and diameter of the rod anode in the membrane-electrode assembly are selected according to desired amounts. Usually, the length thereof is preferably 10-300 mm, and the diameter thereof is preferably 0.5-10 mm. The diameter of the diaphragm in the assembly is regulated so as to be larger by about 0.1-5 mm than the diameter of the rod anode (typically supposed to be a cylinder) disposed in the diaphragm.

The percentage of openings of the porous cathode is preferably 20-80%, and the thickness thereof is preferably 0.1-2 mm.

In the case of using a wire cathode (feeder wire), the diameter thereof is preferably in the range of 0.1-2 mm.

In case where the wire cathode is thinner than that, a voltage loss becomes not negligible due to electrical resistance. Furthermore, such a thin cathode is apt to break in a winding operation because the physical strength thereof is insufficient. In case where the wire cathode is too thick, the movement of the raw material for electrolysis and products of electrolysis from the anode chamber is inhibited, leading to an increase in voltage and a decrease in current efficiency. In addition, such a thick cathode is difficult to wind.

In the case where a wire cathode or a feeder wire is spirally wound on the outer side of the anode and membrane, the wire cathode pitch is preferably about 0.1-10 mm.

When the wire cathode is spirally wound, the angle of winding is governed by the diameter and number of the rod electrode, width of the diaphragm, and diaphragm gap.

The dimensions described above are selected/designed from the standpoints that even when raw water having low conductivity is used, the electrode is in spiral contact with at least part of the membrane to enable electrolysis to proceed smoothly and that the anode chamber formed by the anode and the membrane needs to have a capacity which enables the raw water fed and the gas ingredient evolved to flow smoothly through the anode chamber.

Electrolytic Cell:

At least one of the openings of the anode chamber formed by the anode and the diaphragm in the membrane-electrode assembly has been fixed to a tube connected to a raw-water channel. This tube has almost the same diameter as the tubular diaphragm. The diaphragm and the tube are fixed to each other with an adhesive, and a feeder terminal for the rod anode is connected to the anode in the tube.

Furthermore, a member obtained by fixing tubes respectively to the two anode chamber openings of the assembly may be disposed in a second tube which has at least two openings and is separated from the member. Thus, a cathode chamber can be newly formed between the second tube and the membrane. A feeder terminal for the wire cathode is connected to the cathode in the second tube.

Raw water is fed to one of the openings of the anode chamber and raw water is fed also to one of the openings of the cathode chamber according to need to conduct electrolysis. By conducting electrolysis while feeding raw water to the anode-chamber opening and optionally feeding water also to the cathode-chamber opening, electrolytic water is yielded. Thus, alkaline water and acid water can be simultaneously yielded according to need.

The inner diameter of the second tube forming the cathode chamber is regulated so as to be larger by about 0.1-5 mm than the diameter of the membrane of the assembly. In case where the second tube is thinner than that, substance movement in the catholyte is inhibited and, in particular, there is a possibility that the deposition of hard-water components from, e.g., tap water might be accelerated. On the other hand, in case where the second tube is too thick, the catholyte has a reduced flow rate and the separation and removal of hard-water components by means of a liquid flow rate becomes impossible. This leads to an increase in voltage and a decrease in current efficiency. In addition, the amount of water stored in the cell increases, making it impossible to instantaneously obtain alkaline water.

The material of the second tube preferably is a hydrocarbon resin such as PP, PVC, or PE, a fluororesin, a metal tube, or the like. A tube having heat shrinkability is preferred because the capacity of the electrolytic-cell part can be regulated. The wall thickness of the second tube is preferably smaller from the standpoint of rapidly removing the heat generated in the electrolytic cell. However, the wall thickness thereof is preferably 0.05-2 mm because mechanical strength also is necessary.

The water which is discharged first from the electrolytic cell includes the raw water which has not been sufficiently electrolyzed. In view of this, the amount of the water present in the electrolytic cell and the capacity of the other parts of the piping preferably are smaller.

It is preferred that the two feeder wires extending from the electrodes should be covered with an insulating material in order to prevent the wires from coming into contact with each other. It is preferred that each feeder wire led out of the second tube should be inserted into a covering tube having heat shrinkability and the covering tube be fusion-bonded to the wire to thereby isolate the wire from the electrolytic-water channel in the unit.

In the case of synthesizing ozonized water, too small lengths of the second tube extending from the electrolytic cell to the apparatus outlet are undesirable because the raw water in which the ozone has not sufficiently dissolved is ejected in this case. The longer the gas/liquid contact time, the more the dissolution of the gaseous ozone in the raw water proceeds and the more the efficiency of the synthesis thereof can be increased. It is therefore preferred that the optimal length be regulated so as to result in a contact time in the range of 0.1-10 seconds.

The material of the vessel for storing raw water therein and the material of the piping are selected from ones which are not attacked by raw water. The materials may be a PE resin when there is no particular problem.

With respect to electrolysis conditions, the temperature and the current density preferably are 5-40° C. and 0.01-1 A/cm$^2$, respectively, from the standpoints of the stability and activity of substances yielded.

Raw Water and Electrolytic Water Yielded:

Tap water, well water, or the like can be used as raw water. In this case, it is preferred to pass water through the cathode chamber in order to inhibit the deposition of Ca and Mg. It is also preferred to make the raw water weakly acidic.

Because such water has a low conductivity, there are cases where the resistance loss in the cell voltage is not negligible and it is preferred to increase the conductivity. In this case, it is preferred to dissolve a salt such as $Na_2SO_4$, $K_2SO_4$, NaCl, KCl, or $Na_2CO_3$ as an electrolyte. There are cases where these salts yield a peroxide upon electrolysis and thereby impart the persistence of a sterilizing effect. The concentration thereof is preferably in the range of 0.01-10 g/L. Since an electrode such as, e.g., platinum has the property of increasing in ozone generation efficiency when chloride ions are present, it is preferred to prepare raw water while taking account of that property.

When raw water containing metal ions in a large amount, such as tap water, well water, or seawater, is used, there is a possibility that hydroxides or carbonates might deposit on the surface of the cathode to inhibit reactions. Furthermore, oxides, such as silica, deposit on the anode surface. For eliminating this problem, a reverse current is caused to flow at an appropriate time internal (from 1 minute to 1 hour), whereby acidification and alkalifying occur at the cathode and the anode, respectively. As a result, reactions for removing the deposits readily proceed while being accelerated by gas evolution and the flow of the feed water.

The composition and concentration of the electrolytic water to be yielded can be regulated according to purposes. In the case where the electrolytic water is intended to be used for food treatment, it should be produced as alkaline electrolytic hypochlorite water, slightly acid electrolytic water, or ozonized water. However, in the case where the electrolytic water is intended to be used for sterilization/bleaching, a peroxide may be suitably selected according to the substance to be treated. In the case of hypochlorous acid, the concentration thereof may be 1-100 ppm. Ozonized water may have a concentration of 1-20 ppm. The concentrations of persulfuric acid and percarbonic acid may be 1-100 ppm and 1-100 ppm, respectively.

In the case where hypochlorous acid is to be electrolytically yielded, electrolysis of an acid solution yields hypochlorous acid in a larger amount than a hypochlorite, while use of an alkaline solution yields a hypochlorite in a larger amount than hypochlorous acid. Bactericidal activity varies depending on the nature of the solution. In general, acid solutions often have higher bactericidal activity than alkaline solutions. In the control of, in particular, spores and the like, acid solutions have higher sporicidal activity than alkaline solutions. In contrast, with respect to fungicidal activity, alkaline solutions are more active than acid solutions. It is therefore preferred that the nature of the solution should be suitably regulated so as to be acid or alkaline according to the substance to be treated to thereby impart improved bactericidal or fungicidal activity thereto.

In case where the solution is acidified by adding a strong acid to the solution to excessively enhance acidity, the hypochlorous acid decomposes to generate chlorine gas and, as a result, the oxidizing ability which brings about the bactericidal activity of hypochlorous acid is impaired. For enhancing the bactericidal activity while maintaining the oxidizing ability of the hypochlorous acid, it is preferred to regulate the solution so as to have a pH of 3-7 at 20° C. For regulating the solution so as to have such a pH, it is preferred to use a water-soluble organic weak acid having a low degree of dissociation from the standpoint of ease of pH regulation of the solution. Examples of the water-soluble organic acid include succinic acid, lactic acid, acetic acid, citric acid, and tartaric acid.

For alkalifying the solution, it is preferred to use sodium carbonate, sodium hydrogen carbonate, ammonium carbonate, or the like. Such carbonates are oxidized to percarbonic acid by electrolysis.

A surfactant may be added to the solution in order to further improve bactericidal activity. Addition of a surfactant to the solution not only improves the ability of the solution after electrolysis to wet the substance to be treated therewith, but also improves the affinity of the solution for the cell membranes of mold and germs. Thus, the bactericidal or fungicidal effect further improves.

Usable examples of the surfactant include anionic surfactants such as alkylbenzenesulfonic acid salts and polyoxyethylene alkyl ether sulfuric acid salts, cationic surfactants such as benzalkonium chlorides, amphoteric surfactants such as amine oxides (e.g., alkyldimethylamine oxides), and nonionic surfactants such as polyglycerol fatty acid esters and alkylglycosides. The concentration of the surfactant in the solution is preferably 0.01-10% by weight.

Besides those ingredients, an alcohol may be added to the solution for the purpose of, e.g., improving bactericidal or fungicidal activity and refreshing feeling. Furthermore, additives such as, e.g., a perfume, colorant, bactericide other than surfactants, thickener, enzyme, bleaching agent, chelating agent, electrolyte other than chlorine compounds, builder, antiseptic, and rust preventive may be added according to need. It is especially preferred from the standpoint of storage stability that the water to be electrolyzed should contain an antiseptic.

Electrolytic-Water Sprayer (Trigger Spray):

The electrolytic-water sprayer includes a vessel for containing raw water therein and a head connected to the upper opening of the vessel. Although the vessel may be either rigid or flexible, it is preferred that the vessel should be made of a rigid material selected from, e.g., various rigid resins, metals, glasses, and ceramics. The capacity of the vessel is preferably about 10-1,000 mL, more preferably 200-500 mL.

The trigger spray has been fixed to a head in which a battery can be housed. The apparatus may be equipped with a device which generates power for electrolysis upon trigger operation, without employing a battery as a power source. In place of using a simple primary battery, use may be made of a secondary battery or capacitor, which is rechargeable. It is also possible to operate the apparatus with an adapter capable of supplying DC power from an AC power source.

The values of the voltage and current to be applied are suitably determined according to the concentration suitable for obtaining given bactericidal activity suitable for the substance to be deodorized, sterilized, or otherwise treated and to the volume of the solution to be electrolyzed. One trigger operation results in the ejection of 0.1-1 cc, and a voltage of about 3-40 V is applied between the electrodes. A device for changing the voltage to be applied to the electrodes may be disposed in the circuit.

A switch for initiating/terminating voltage application to the electrodes has been disposed in the trigger spray so that a voltage is applied only when the apparatus is in use, i.e., pulling the trigger automatically results in switching on and returning the trigger results in switching off.

The electrolytic-water sprayer may have a device which generates power for electrolysis upon a production operation. Examples of this device include a motor which interlocks with the trigger. This motor is usually disposed in the trigger spray.

The electrolytic-water sprayer can have means for indicating that electrolysis is being conducted. Examples of the means include an LED lamp which is made on during voltage application by a trigger operation. A function may be added which switches off the LED lamp when a specified current does not flow due to, e.g., battery exhaustion.

The electrolytic-water sprayer works by the following mechanism. The sprayer is switched on by a trigger operation to cause a current to flow through the circuit. As a result, the current flows through the electrodes. In this operation, the raw water present in the tube is electrolyzed almost instantaneously and ejected or sprayed outward through the nozzle of the head by a piston/cylinder mechanism. Namely, in this sprayer of the invention, electrolysis is conducted simultaneously with a production operation (e.g., trigger operation). It is preferred that electrolytic water should begin to be yielded by electrolysis within 1 second after the initiation of a trigger operation.

Besides the embodiment shown in figures, there are various embodiments of the electrolytic-water sprayer equipped with a trigger spray. Furthermore, there are trigger sprays having various mechanisms. The trigger sprays differ in the liquid passage therein, the position of the fulcrum of the trigger, etc. according to the mechanisms. However, any desired trigger spray can be employed in the sprayer of the invention.

Next, the electrolytic-water sprayer of the invention is explained with respect to the embodiment shown in figures.

Figure 2:
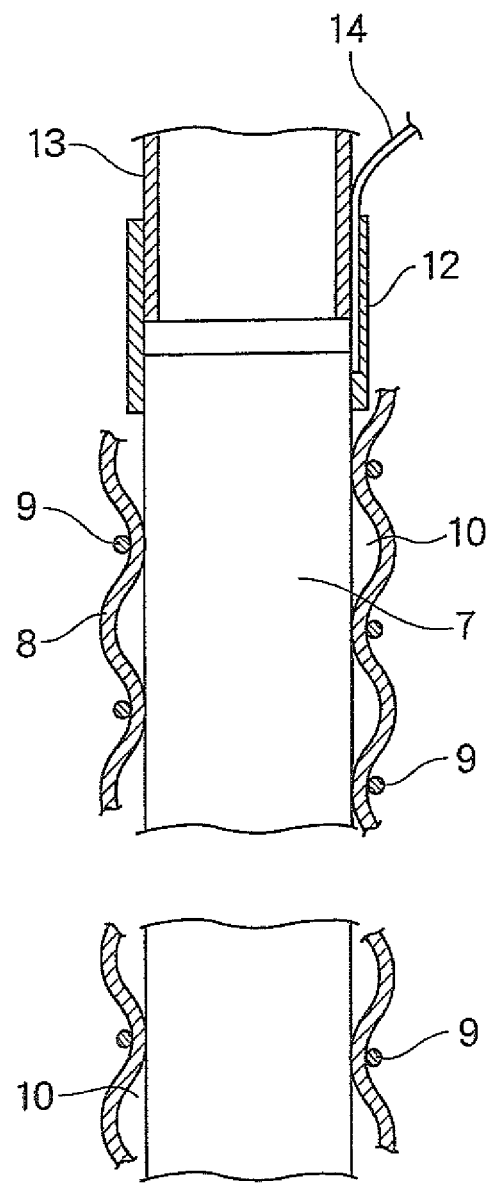
FIG. 2 is an exploded enlarged view of an important part of the sprayer shown in FIG. 1.
Figure 3:
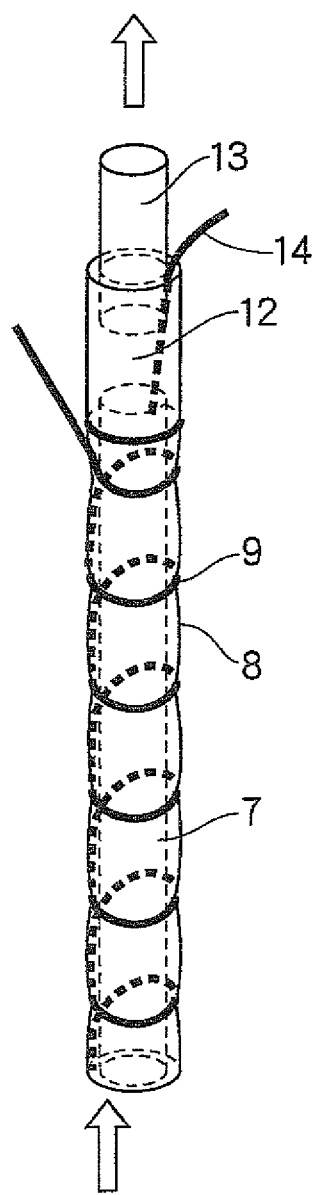
FIG. 3 is a slant view of the electrolytic cell shown in FIGS. 1 and 2.

FIG. 1 is a front view illustrating an electrolytic-water sprayer as one embodiment of the invention. FIG. 2 is an exploded enlarged view of an important part of the sprayer shown in FIG. 1. FIG. 3 is a slant view of the electrolytic cell shown in FIGS. 1 and 2. The electrolytic-water sprayer (trigger spray) 1 shown in FIG. 1 includes a vessel 3 for containing raw water 2 and a head 4 connected to the upper opening of this vessel 3. The raw water 2 may be pure water or may be one containing one or more electrolytes dissolved therein, such as, e.g., sodium chloride, potassium chloride, and magnesium chloride.

In the vessel 3 has been disposed an electrolytic cell 6 composed of an anode, a cathode, and a diaphragm. As shown in FIG. 2, this electrolysis cell 6 is constituted of: an anode 7 which is a metallic rod electrode on which a catalyst has been deposited; a diaphragm 8 which is a tubular ion-exchange membrane wound around the anode 7; and a wire cathode 9 which is a metallic wire wound around the diaphragm 8. This diaphragm 8 is obtained by rolling a square sheet so as to have a circular shape when viewed from above and bonding two end parts along the lengthwise direction.

The diaphragm 8 intrinsically has no recesses/protrusions. However, by winding the wire cathode 9 on the diaphragm 8, that part of the diaphragm 8 which is in contact with the wire cathode 9 is strongly pushed against the anode 7, and that part of the diaphragm 8 which is not in contact with the wire cathode 9 is bent outward to form a spiral anode chamber 10 between the anode 7 and the diaphragm 8.

Furthermore, that space in the vessel 3 which is on the outer side of the diaphragm 8 constitutes a cathode chamber.

A tube for feeder wire holding 13 has been connected to the upper end of the rod anode 7 through a cylindrical connecting tube 12 having a short length. A feeder wire 14 is held between the inner surface of the connecting tube 12 and the outer surface of the tube for feeder wire holding 13, and an end of the feeder wire 14 has been connected to an upper end part of the anode 7.

The upper end of the tube for feeder wire holding 13 has been fitted into a vertical pipeline 15 in the head 4, and the upper end of the vertical pipeline 15 is communicatively connected to a horizontal pipeline 16 in the head 4.

At the other end of the horizontal pipeline 16 has been disposed a spray nozzle 17. A fulcrum 19 of a trigger arm 18 has been disposed on the slightly inner side of the spray nozzle 17 so that the trigger arm 18 is swingably movable around the fulcrum 19. The trigger arm 18 has been connected to a piston rod 20 extending inward so that the piston rod 20 travels in a cylinder 21 according to the movement of the trigger arm 18.

Numeral 22 denotes a trigger-engaged switch disposed so as to be in contact with the trigger arm 18; 23 denotes a power source battery disposed in the head 4; and 24 denotes an LED which is on only when electrolysis is proceeding.

The electrolytic-water sprayer 1 having such constitution is held in a hand, and an inward force is applied to the trigger arm 18 with the forefinger and middle finger. As a result, the trigger arm 18 moves around the fulcrum 19, whereby the trigger-engaged switch 22 becomes on and a voltage is applied to the electrolytic cell 6. Simultaneously therewith, the piston in the cylinder 21 moves to bring the raw water 2 present in the vessel 3 into contact with the electrolytic cell 6, where this raw water 2 is electrolyzed to yield electrolytic water. The anode 7 in this electrolytic cell 6 has a catalyst, such as, e.g., a layer of conductive diamond, deposited on the surface thereof. Thus, electrolytic water containing ozone or other active species dissolved therein in a high concentration is obtained. Since a spiral anode chamber 10 has been formed inside the diaphragm 8 in this electrolytic cell 6, an appropriate gas/liquid passage is formed in the anode chamber. Consequently, the concentration of an electrolytically yielded species in the electrolytic water can be regulated to a desired value by changing the water feed rate and current value.

The electrolytic water yielded passes instantaneously through the vertical pipeline 15 and horizontal pipeline 16 and is sprayed through the spray nozzle 17 on a substance to be sterilized, together with air introduced through an outside-air intake opening not shown.

Figure 4:
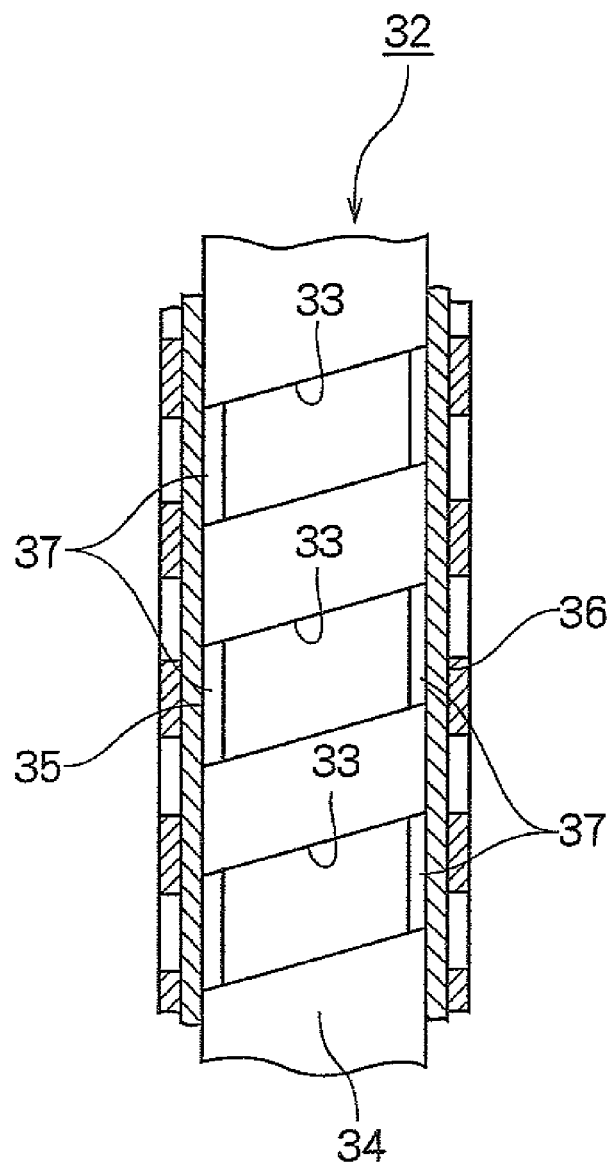
FIG. 4 is a partial sectional view illustrating another embodiment of the electrolytic cell of the invention.

FIG. 4 is a partial sectional view illustrating another electrolytic cell according to the invention. This figure shows an embodiment employing a porous cathode and an anode to which recesses and protrusions have been imparted.

The electrolytic cell 32 is constituted of an anode (rod electrode), a cathode (counter electrode), and a diaphragm. This electrolytic cell 32 is composed of: an anode 34 which is a metallic rod electrode having a spiral groove 33 formed in the periphery thereof; a diaphragm 35 which is an ion-exchange membrane formed into a tubular shape and disposed around the periphery of the anode 34; and a porous cathode 36 having the shape of a metal gauze, expanded mesh, or punching metal and disposed around the periphery of the diaphragm 35.

Unlike the embodiment shown in FIGS. 1 to 3, this embodiment is substantially free from deformation of the diaphragm 35 toward the anode 34 by the porous cathode 36. However, since the anode 34 has a groove 33 formed in the periphery thereof, this embodiment has an anode chamber 37 formed between that part of the diaphragm 35 which corresponds to the groove 33 and the anode 34.

In this embodiment also, an appropriate gas/liquid passage is formed in the anode chamber, and the concentration of an electrolytically yielded species in the electrolytic water can be regulated to a desired value by changing the water feed rate and current value.

The embodiment in which the anode has recesses and protrusions should not be construed as being limited to that having the groove. Although the embodiment explained above employs a rod-form or tubular anode having a circular shape when viewed from above, the shape of the anode is not limited thereto. For example, the anode may have shapes such as those shown by the plan views in FIGS. 5 and 6. The diaphragm 41 in FIG. 5 has a vertically tubular form obtained by rolling a square sheet and bonding overlap parts 42 of the two ends to each other. The rod anode 43 has protrudent parts 44 projected outward respectively in six parts of the base in a solid cylinder form. The tubular diaphragm 41 has been stretched on and around the six protrudent parts 44. Six anode chambers 45 in total have been thus formed between the diaphragm 41 and the anode 43.

Figure 6:
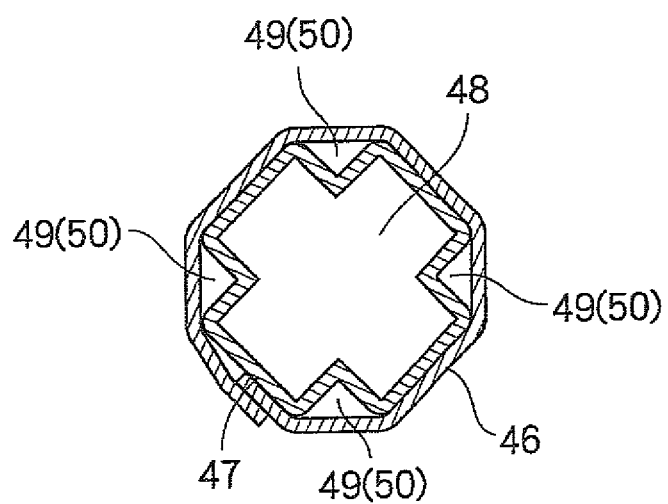
FIG. 6 is a plan view of a tubular anode.

In the case of FIG. 6 also, the diaphragm 46 has a vertically tubular form obtained by rolling a square sheet and bonding overlap parts 47 of the two ends to each other. The tubular anode 48 has a shape obtained from a prismatic base by forming a recessed part 49 depressed inward at each of the four corners. The tubular diaphragm 46 has been stretched on and around a total of eight base parts of the four recessed parts 49. Anode chambers 50 corresponding to the shapes of the recessed parts 49 are formed between the diaphragm 46 and the anode 48.

Figure 7:
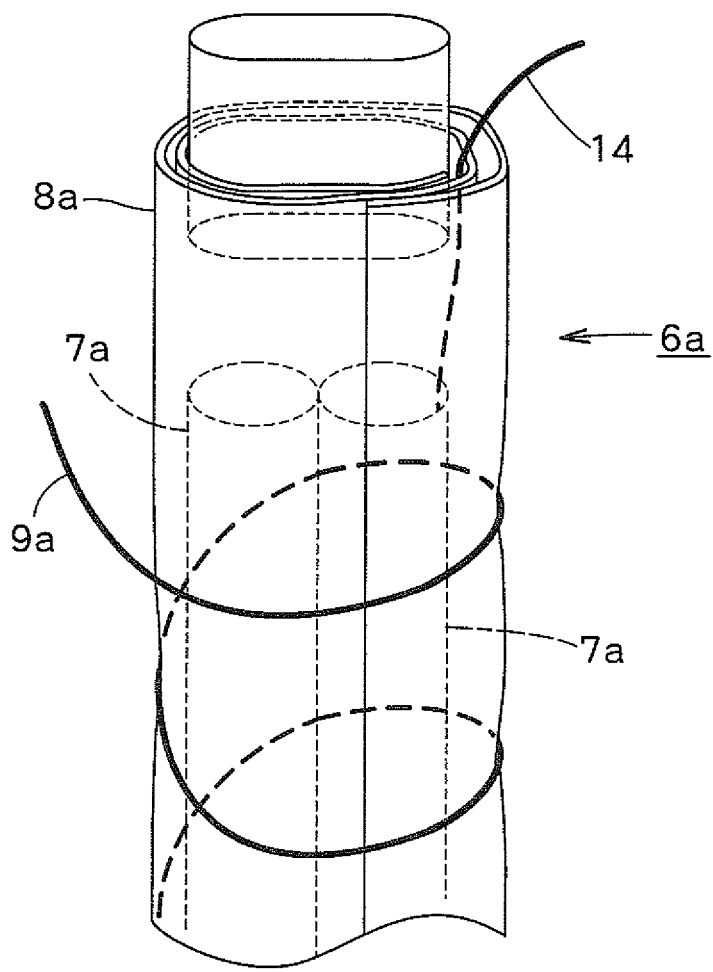
FIG. 7 is a partial slant view illustrating a still other embodiment of the electrolytic cell of the invention.
Figure 8:
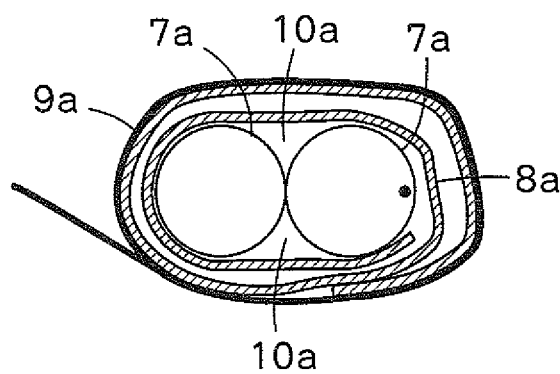
FIG. 8 is a transverse sectional view of the electrolytic cell of FIG. 7.

FIG. 7 is a partial slant view illustrating a still other embodiment of the electrolytic cell of the invention, and FIG. 8 is a transverse sectional view of the electrolytic cell of FIG. 7. This embodiment relates to an improvement of the embodiment shown in FIGS. 1 to 3, and explanation of common members will be omitted by assigning the same reference numerals.

In the electrolytic cell 6a shown in FIGS. 7 and 8, two rods of anodes made of niobium and covered with a conductive-diamond catalyst on the surface thereof are wrapped by an ion-exchange membrane 8a so as to form two layers of the membrane in tubular form, and a stainless wire serving as a cathode 9a is spirally wound on the membrane to thereby form an anodes-membrane-cathode assembly (electrolytic cell).

According to this embodiment, as shown in FIG. 8, the anodes 7a are in rod-form, and a relatively large space is formed between the two anodes 7a each having a curved surface. In addition, a relatively large space is also formed between the anodes 7a and the ion-exchange membrane 8a. These spaces function as an anode chamber 10a, and electrolytic water passes through this anode chamber 10a.

Figure 5:
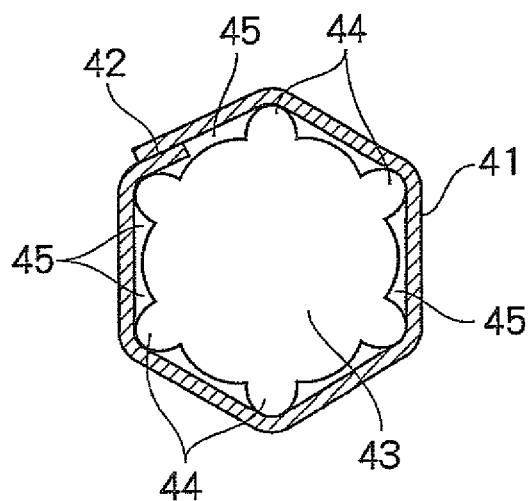
FIG. 5 is a plan view of another rod anode.

According to this embodiment, cost- and time-consuming processing of the anode per se is not required unlike the embodiment as shown in FIGS. 4 to 6. Despite that, this embodiment provides an anode chamber having a volume equal to or rather larger than that in the embodiment of FIGS. 4 to 6.

EXAMPLES

Examples concerning the production of electrolytic water according to the invention will be given below. However, the invention should not be construed as being limited to the following Examples. The ozone concentration, hypochlorous acid concentration, persulfuric acid concentration, and percarbonic acid concentration in each Example were determined with an ultraviolet spectrophotometer and by iodometry using potassium iodide.

Example 1

A rod made of niobium (diameter, 2 mm) on which a conductive-diamond catalyst (dopant boron concentration, 2,500 ppm) had been deposited was placed as an anode in a tubular ion-exchange membrane (Nafion 350, manufactured by DuPont; thickness, 0.35 mm; diameter, 3 mm). A commercial platinum wire (diameter, 0.4 mm) was spirally wound as a cathode on the diaphragm to obtain an anode-membrane-cathode assembly. The winding pitch was 4 mm. Tubes (diameter, 4 mm) were bonded to upper and lower parts of the assembly, and feeder wires from a DC power source were connected to the respective electrodes to obtain an electrolytic cell. Pure water was passed upward through the anode chamber at a rate of 40 cc/min. Currents of 0.5 A and 1 A were separately caused to flow. As a result, the cell voltages were 13 V and 19 V, respectively, the ozonized water concentrations were 8 ppm and 21 ppm, respectively, and the ozone generation efficiencies were 13% and 12%, respectively, in these operations. The temperature of the water at the outlet was about 30° C.

This electrolytic cell was connected in a trigger type sprayer shown in FIG. 1 to a PE resin tube attached to the intake. A battery was mounted in the head of the trigger type sprayer. In a circuit part, the electrode terminals were connected to a variable resistor and a switch with a wiring. The vessel was filled with 500 cc of pure water.

The trigger was pulled, upon which the circuit was switched on and a current flowed between the battery and the cell. Simultaneously therewith, pure water was ejected. The amount of the pure water ejected was about 0.5 cc, and the quantity of electricity which flowed during this operation was 0.25 C (0.5 s×0.5 A). The terminal voltage of the cell was 13 V. The operation was repeatedly conducted 100 times. As a result, the ozone concentration in the solution ejected, which amounted to about 50 cc, was 8 ppm. The trigger operation was repeated 2,000 times, and the concentration of the ozonized water obtained thereafter remained at about 8 ppm.

Comparative Example 1

The same materials as in Example 1 were used. A strip of the ion-exchange membrane was spirally wound on the anode, and the platinum wire was wound on the diaphragm to obtain an anode-membrane-cathode assembly. Pure water was passed upward at a rate of 40 cc/min through an electrolytic cell in which the membrane-electrode assembly had been mounted. Currents of 0.5 A and 1 A were separately caused to flow. As a result, the oxygen and ozone generated at the anode were mixed with the hydrogen gas generated at the cathode because the diaphragm had been disposed spirally, and electrolytic water containing these gases dissolved therein was yielded. In these operations, the cell voltages were 10 V and 13 V, respectively, the ozonized water concentrations were 5 ppm and 9 ppm, respectively, and the ozone generation efficiencies were 8% and 5%, respectively.

Example 2

Those parts of the membrane in the assembly of Example 1 which constituted the two openings of the anode chamber were fixed to tubes having a diameter of 4 mm. The resultant member was disposed in a second tube having an inner diameter of 5 mm to form a cathode chamber between the second tube and the membrane. A feeder terminal for the wire cathode was connected to the cathode in the second tube. A 2 g/L aqueous solution of sodium chloride was fed to the anode chamber at a rate of 40 cc/min, and water was fed also to the cathode chamber in the same manner. A current of 1 A was caused to flow. As a result, alkaline water containing hydrogen and having a pH of 11 and acid water containing hypochlorite ions in an amount of 40 ppm could be simultaneously yielded.

Example 3

The same test as in Example 2 was conducted, except that tap water was fed to the anode chamber and the cathode chamber. As a result, the ozonized water yielded at 0.5 A had a concentration of 4.5 ppm (current efficiency, 7.3%).

Comparative Example 2

The same test as in Comparative Example 1 was conducted, except that tap water was used as a raw material. As a result, the ozonized water yielded at 0.5 A had a concentration of 1.5 ppm (current efficiency, 2.4%).

Example 4

A round rod made of titanium which had a platinum layer formed thereon (20 g/m$^2$) was used as an anode to produce the same assembly as in Example 1. Using tap water as a raw material, the same test as in Example 3 was conducted. As a result, the cell voltage at 0.5 A was 12 V, and the ozonized water had a concentration of 0.5 ppm.

Example 5

Two rods made of niobium (diameter, 2 mm) on which a conductive-diamond catalyst had been deposited (dopant boron concentration, 1,000 ppm) as anodes were wrapped by an ion-exchange membrane (Nafion 324, manufactured by DuPont; thickness, 0.35 mm; diameter, 3 mm) so as to form two layers of the membrane in tubular form, and a stainless wire (diameter, 0.5 mm) serving as a cathode is spirally wound on the membrane to thereby obtain an anodes-membrane-cathode assembly as shown in FIGS. 7 and 8. The winding pitch was 2 mm.

Tubes (diameter, 4 mm) were bonded to upper and lower parts of the assembly, and feeder wires from a DC power source were connected to the respective electrodes to obtain an electrolytic cell. Pure water was passed upward through the anode chamber at a rate of 40 cc/min. Currents of 0.5 A and 1 A were separately caused to flow. As a result, the cell voltages were 13 V and 19 V, respectively, the ozonized water concentrations were 15 ppm and 17 ppm, respectively, and the ozone generation efficiencies were 13% and 15%, respectively, in these operations. The temperature of the water at the outlet was about 30° C. Water leakage from the tubular membrane scarcely occurred.

While the present invention has been described in detail and with reference to specific embodiments thereof, it will be apparent to one skilled in the art that various changes and modifications can be made therein without departing from the spirit and scope thereof.

This application is based on Japanese Patent Application Nos. 2007-296769 (filed Nov. 15, 2007) and 2008-266158 (filed Oct. 15, 2008), and the contents thereof are herein incorporated by reference.

What is claimed is:

1. An electrolytic cell which comprises:
    a membrane-electrode assembly, which comprises an electrode chamber having at least one opening;
    a feeder wire-fixing tube fitted to the at least one opening of the electrode chamber of the membrane-electrode assembly;
    a feeder wire fixed between the at least one opening and the feeder wire-fixing tube,
    wherein the membrane-electrode assembly comprising at least one rod-form electrode placed in a diaphragm which is preformed into a tube, thereby forming a tubular diaphragm;
    the tubular diaphragm disposed around the periphery of the rod-form electrode; and
    a wire-form counter electrode spirally wound around the periphery of the tubular diaphragm,
    the tubular diaphragm being fixed to the rod-form electrode with the wire-form counter electrode so that the tubular diaphragm is in contact with at least a part of the rod-form electrode and the tubular diaphragm is in contact with at least a part of the wire-form counter electrode to thereby form the electrode chamber,
    the electrode chamber having a spiral shape and having a gas/liquid passage between the tubular diaphragm and the rod-form electrode,
    wherein the rod-form electrode is an anode and the counter electrode is cathode,
    wherein the rod-form electrode comprises diamond, and
    wherein the wire-form counter electrode is spirally wound at a pitch of 1-10 mm.

2. The electrolytic cell of claim 1, wherein the membrane-electrode assembly comprises a plurality of rod-form electrodes.

3. The electrolytic cell of claim 1, wherein a tube for forming a tubular counter electrode chamber is disposed around the electrode chamber and the counter electrode.

4. The electrolytic cell of claim 1, which yields electrolytic water, the electrolytic water comprising ozonized water as a main component.

5. The electrolytic cell of claim 3, which yields electrolytic water, the electrolytic water comprising ozonized water as a main component.

\* \* \* \* \*